(12) United States Patent
Johnson et al.

(10) Patent No.: US 8,540,771 B2
(45) Date of Patent: Sep. 24, 2013

(54) PROSTHESES FOR SPINE DISCS HAVING FUSION CAPABILITY

(75) Inventors: Wesley M. Johnson, Tampa, FL (US); Thomas B. Freeman, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/367,621

(22) Filed: Feb. 7, 2012

(65) Prior Publication Data

US 2012/0136447 A1  May 31, 2012

Related U.S. Application Data

(62) Division of application No. 11/222,880, filed on Sep. 9, 2005, now Pat. No. 8,110,003.

(60) Provisional application No. 60/608,209, filed on Sep. 9, 2004.

(51) Int. Cl.
*A61F 2/44* (2006.01)

(52) U.S. Cl.
USPC .................................. 623/17.11; 623/17.12

(58) Field of Classification Search
CPC .................................................. A61F 2/4611
USPC ........................................ 623/17.11, 17.12
See application file for complete search history.

(56) References Cited

U.S. PATENT DOCUMENTS

| | | | |
|---|---|---|---|
| 3,867,728 A * | 2/1975 | Stubstad et al. | 623/17.16 |
| 4,349,921 A | 9/1982 | Kuntz | |
| 4,911,718 A | 3/1990 | Lee et al. | |
| 5,071,437 A | 12/1991 | Steffee | |
| 5,192,326 A | 3/1993 | Bao et al. | |
| 5,545,229 A | 8/1996 | Parsons et al. | |
| 5,674,295 A | 10/1997 | Ray et al. | |
| 5,893,889 A | 4/1999 | Harrington | |
| 6,022,376 A | 2/2000 | Assell et al. | |
| 6,039,763 A | 3/2000 | Shelokov | |
| 6,093,205 A | 7/2000 | McLeod et al. | |
| 6,156,067 A | 12/2000 | Bryan et al. | |
| 6,402,784 B1 | 6/2002 | Wardlaw | |
| 6,579,320 B1 | 6/2003 | Gauchet et al. | |
| 6,582,466 B1 | 6/2003 | Gauchet | |
| 6,602,291 B1 | 8/2003 | Ray et al. | |
| 6,869,445 B1 * | 3/2005 | Johnson | 623/17.11 |
| 6,881,228 B2 | 4/2005 | Zdeblick et al. | |
| 2002/0116070 A1 | 8/2002 | Amara et al. | |
| 2002/0183848 A1 | 12/2002 | Ray et al. | |

(Continued)

OTHER PUBLICATIONS

International Search Report with a mail date of Nov. 22, 2006 for related international patent application No. PCT/US05/32286 with an international filing date of Sep. 9, 2005.
Masahiko et al., Bone Ingrowth Fixation of Artificial Intervertebral Disc Consisting of Bioceramic-Coated Three-dimensional Fabric. Spine, 2003, vol. 28, No. 7, pp. 637-644.

(Continued)

*Primary Examiner* — Jason-Dennis Stewart
(74) *Attorney, Agent, or Firm* — Andriy Lytvyn; Smith & Hopen, P.A.

(57) ABSTRACT

The present invention provides both a device and a method. The device is a human made replacement for the soft discs in the spine. A fabric pouch encloses a central hydraulic element made up of small soft beads. Two pouches with beads are implanted into a prepared disc space to function as an intervertebral disc. The method is conversion of the device into a fusion element.

7 Claims, 4 Drawing Sheets

(56) References Cited

U.S. PATENT DOCUMENTS

| | | |
|---|---|---|
| 2003/0100951 A1 | 5/2003 | Serhan et al. |
| 2003/0191536 A1 | 10/2003 | Ferree |
| 2003/0199982 A1 | 10/2003 | Bryan |
| 2004/0010317 A1 | 1/2004 | Lambrecht et al. |
| 2004/0230309 A1 | 11/2004 | DiMauro et al. |
| 2005/0055096 A1 | 3/2005 | Serhan et al. |

OTHER PUBLICATIONS

Kadoya et al., Biomechanical and Morphologic Evaluation of a Three-Dimensional Fabric Sheep Artificial Intervertebral Disc. Spine, 2001, vol. 26, No. 14, pp. 1562-1569.

Yoshihisa et al., Artificial Intervertebral Disc Replacement Using Bioactive Three-Dimensional Fabric. Spine, 2002, vol. 27, No. 9, pp. 929-936.

* cited by examiner

PROSTHESES FOR SPINE DISCS HAVING FUSION CAPABILITY

CROSS-REFERENCE TO RELATED APPLICATIONS

This application is a divisional application of U.S. application Ser. No. 11/222,880, entitled "Prostheses for Spine Discs Having Fusion Capability", filed on Sep. 9, 2005, which claims priority to U.S. Provisional Patent Application No. 60/608,209, filed Sep. 9, 2004, the contents of which are herein incorporated by reference.

BACKGROUND OF INVENTION

Degenerative disc disease results in significant pain for a large population of patients. The current standard of care is an instrumented fusion using a variety of surgical approaches. In the procedure, the intervertebral disc is removed (discectomy) and replaced with a stiff strut or cage. Many times, additional plates, rods and screws are used to stabilize the construct as it heals. The healing process has the goal of vertebral body bony fusion across the disc space. In some cases, as many as 20%, fusion does not occur. Instrumentation, such as cages and screws and rods can migrate, causing serious neurological complications. In patients who smoke, fusion success is even smaller. For those patients in whom fusion was successful, there appears to be a greater likelihood of adjacent disc failure. While this has not been conclusively proven, it is clear that the adjacent levels are subject to higher stresses due to loss of range of motion at the fused disc. Additionally, there is a loss of mobility at the fused level that varies with location in the spine.

Another segment of the population suffers from spine deformities such as scoliosis. Scoliosis is also a degenerative disease in that the spine curvature progresses and may result in cardiopulmonary distress.

In some patients treatment of degenerative disc disease with a prostheses may not be tolerated or the device may fail. In those cases the implanted device should have a strategy for conversion to fusion.

Many of the current devices used in spine disc replacements can be characterized as being generally stiff. These devices are often fabricated from metals and plastics. Some may include a softer core element. U.S. Pat. No. 6,881,228 B2 to Zdeblick teaches an artificial disc implant having for replacing the spinal disc between two vertebrae of the spine. The implant employs an upper and lower shell with a spacer sandwiched in the space there between. The upper and lower shells are composed of rigid materials and generally use ribbed protrusions at the vertebral interfaces. The spacer utilizes a hydrogel substance within a single cavity. At insertion the hydrogel substance is maintained in a dehydrated state to reduce the volume of the spacer thereby facilitating insertion into the vertebral space. Following insertion the hydrogel is rehydrated. These inflexible devices are generally difficult to insert and require insertion via an anterior insertional approach. Moreover, as a result of their rigid shape they are generally unable to adopt a shape conforming to the environment into which they have been inserted.

Due to the inherent limitations of an inflexible disc, a new generation of more flexible replacement discs has been developed. These prosthetic spinal disc replacements have flexible coverings surrounding a dehydrated hydogel core. U.S. Pat. No. 6,602,291 B1 to Ray et al. teaches a prosthetic spine disc nucleus for implantation into a nucleus cavity of a spinal disc. The prosthetic device is a constraining jacket of flexible but inelastic composition surrounding a single hydrogel core. The device is implanted in a dehydrated state with a fixed quantity of hydrogel contained within the jacket. By virtue of its dehydrated state, the size of prosthesis is reduced, thereby facilitating its insertion and enabling the device to be implanted via a posterior insertional approach. Following implantation the hydrogel core expands from a dehydrated state to a hydrated state. This prosthetic device is designed to replace only the nucleus of the disc rather than the entire disc. Furthermore, while addressing issues related to motion restoration or preservation, these devices do not address the need of subsequent conversion to a fusion mass should the biomechanical behavior of the device degrade with time.

Accordingly, what is needed in the art is a total disc replacement that restores normal biomechanical behavior while eliminating pain, restoring full function of the spine, provides a treatment for deformity, and has a strategy for conversion to fusion.

SUMMARY OF INVENTION

In accordance with the present invention, a disc replacement is provided to replace a damaged disc to restore normal biomechanical behavior that eliminates pain and restores full function. Current devices are generally fabricated from metals and plastics. The present invention is a compliant element with two phases. One phase is the exterior and is fibrous while the second phase is interior and hydraulic in nature. These two phases provide for containment of the hydraulic phase and natural elastic response.

An additional containment membrane may be used to regulate the hydration rate of the hydraulic element and minimize migration of the hydraulic element(s).

In addition, treatment of the surfaces of the outer superior and inferior element surfaces enhances a bony union between the invention and host vertebral body endplates.

The present invention will therefore be biologically incorporated to provide fixation to the superior and inferior vertebral bodies. Additional initial fixation may include staples, screws, nails or other mechanical fastening methods and/or biocompatible adhesives.

Two devices are contemplated with one on each lateral side for all disc replacements. For treating certain deformities, such as scoliosis, the two devices will contain unequal amounts of hydraulic element with one larger thereby counteracting the natural scoliotic curve. The hydraulic element can be added before, during or after surgery.

It is not uncommon for the biomechanical behavior of a disc replacement to degrade over time, or for the device not to perform as expected in any given patient. The current surgical strategy in these cases is to remove the disc and fuse the vertebra. Fusing the vertebra places additional stress on the adjacent discs, which can result in early failure, and limits patient flexibility.

A major benefit of the present invention is the ability to convert the device to a fusion element. No existing or contemplated disc prosthetic devices disclose a method for salvage, revision, or conversion to fusion. The device in accordance with the present invention may need to be converted to fusion mass if its biomechanical behavior degrades over time. Additionally, there are many reasons why one device or another does not perform as expected in any given patient. Many of the reasons are not understood. Current disc prostheses designs generally require physical removal and subsequent revision or replacement with a standard fusion procedure. Such procedures are costly in terms of morbidity and money. The present invention allows for percutaneous injection of bone forming materials into the device, allowing bone to form between the adjacent vertebral bodies forming a bony fusion. Removal of some or substantially all the hydraulic element may be accomplished through aspiration or suction or by other endoscopic means, leaving the fabric intact. Removal of hydraulic element materials may be necessary to allow room for the bone forming materials. The bone forming materials are all those known in the medical arts, including, but not limited to, bone morphogenic proteins (BMP), demineralized bone matrix (DBM), aspirated autologous bone marrows, natural and synthetic calcium phosphates, or other osteoinductive, osteoconductive, structural or stem cell elements alone or in combination. The formulation of bone forming materials is such that immediate or rapid structural stability is provided to minimize relative motion between the device and the bone forming materials. To accomplish this, one or more bone forming materials are injected, at the same or different time as the other materials, which harden after a relatively short cure time. The patient is immobilized during the curing or healing period. The existence of an effective disc prostheses and facet replacement together, as described by the present invention, will radically change the surgical strategy currently in use, possibly eliminating spine fusion altogether.

Additionally, the device in accordance with the present invention is implanted posteriorly, while the current generation of disc prostheses in trials are implanted anteriorly. The posterior approach means less muscle disruption, less pain from the operation, shorter operating time, less cost, less blood loss, and overall less morbidity. Additionally, the device can be implanted endoscopically, reducing morbidities and operation time even further.

As such, the present invention provides both a device and a method. The device is a human made replacement for the soft discs in the spine. A fabric pouch encloses a central hydraulic element made up of small soft beads. The pouch with the beads is implanted into a prepared disc space to function as a disc. The method is conversion of the device into a fusion element.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The present invention is a medical device and method. The device consists of two implantable parts. the two parts of the device will be implanted in a disc space after discectomy. The surgical approach can be posterior or anterior, although posterolateral is preferred. The device will be of a size to be implanted in a minimally invasive or endoscopic manner. The device is dry prior to implantation and fits into a space approximately 9 mm by 12 mm long. After positioning in the disc space and possible use of initial fixation, the device is saturated with normal saline and the incision closed. Post operatively, the hydraulic element absorbs water and swells to several times their dry size. The hydraulic element may be added before, during or after the operation. Addition of hydraulic element to one of the two devices may be made to provide asymmetry for correction of spine deformities, such as scoliosis.

Figure 1:
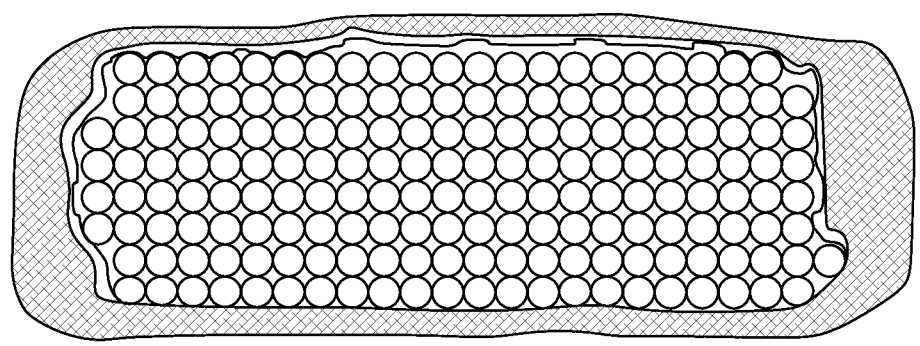
FIG. 1 is an illustrative lateral bisectional view of the disc prosthesis in accordance with the present invention.
Figure 2:
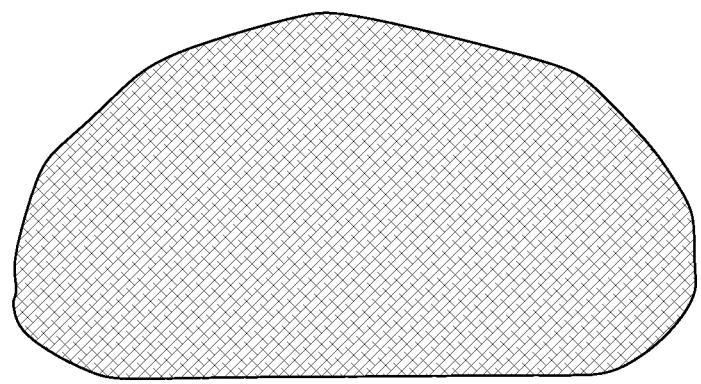
FIG. 2 is an illustrative superior end view of the disc prosthesis in accordance with the present invention.

With reference to FIG. 1 and FIG. 2, in accordance with one embodiment, the invention is a pair of fabric devices with a hydraulic element in the center of each that replaces the natural disc. The hydraulic element in each device consists of many small beads. The hydraulic element consists of an elastic material such as, but not limited to, polyvinyl alcohol, or other hydrogel, or material of a biological origin, in the form of beads or in liquid form. The beads can be implanted in the fabric containment at any time including at time of manufacture or pre-operatively, interoperatively, or post-operatively with a syringe like instrument. Beads are placed or injected into the fabric retainer interior in a dehydrated state. The beads hydrate increasing their size several fold eliminating the likelihood of migrating out of the fabric retainer. Additionally, a porous membrane (FIG. 1) may also be used to control the rate of hydraulic element hydration and minimize the likelihood of bead migration and expulsion. Other materials such as temperature sensitive gels may be used and injected into the fabric retainer interior. The injected liquid transforms into a hydraulic gel on exposure to physiologic temperature. The fabric is woven and/or layered and provides confinement of the hydraulic element beads. The fabric constituents are those known in the medical arts including polyethylene, polytrifluorethylene, polypropylene, and biological fibers (natural or synthetic) and constructs. Configurations of fabric can be of any orientation. The fabric strands may be all aligned or at any relative angle to each other and the axis of the intended disc space location. The fabric element may contain internal compartments. The compartments can function to separate the hydraulic element subcomponents into sections. Each section could contain a different quantity of hydraulic element thereby providing a different stiffness in each section.

Figure 3:
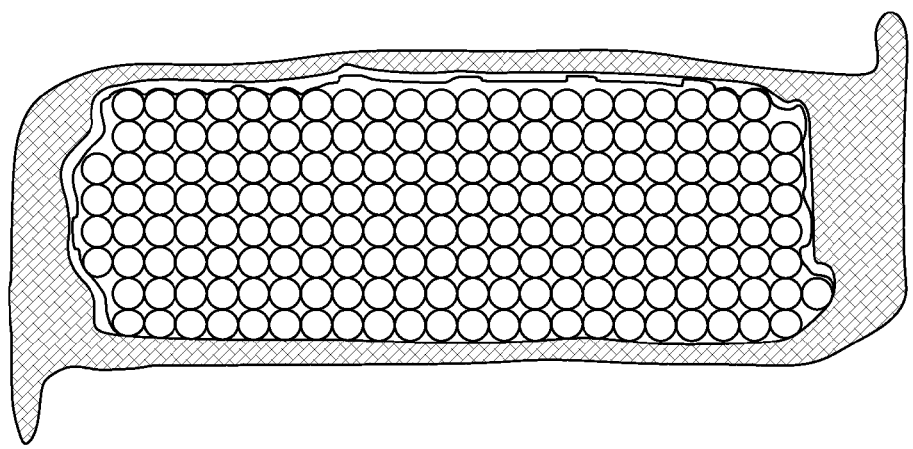
FIG. 3 is an illustrative lateral bisectional view of the disc prosthesis, showing fixation tabs, in accordance with the present invention.
Figure 4:
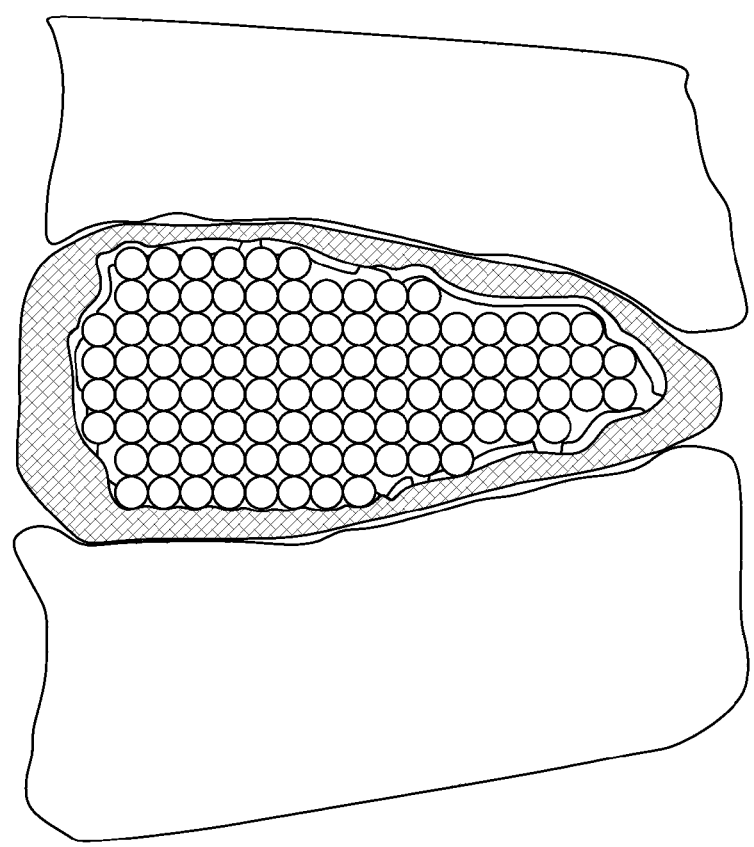
FIG. 4 is an illustrative lateral bisectional view of the disc prosthesis showing the placement of the device relative to the spine, in accordance with the present invention.
Figure 5:
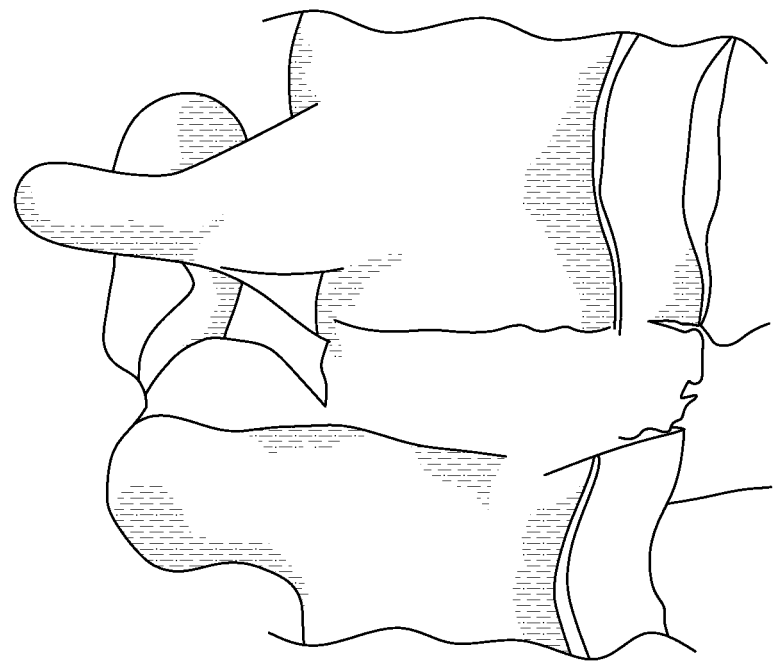
FIG. 5 is an illustrative view of the conceptual model shown between 2 plastic vertebral bodies in accordance with the present invention.
Figure 6:
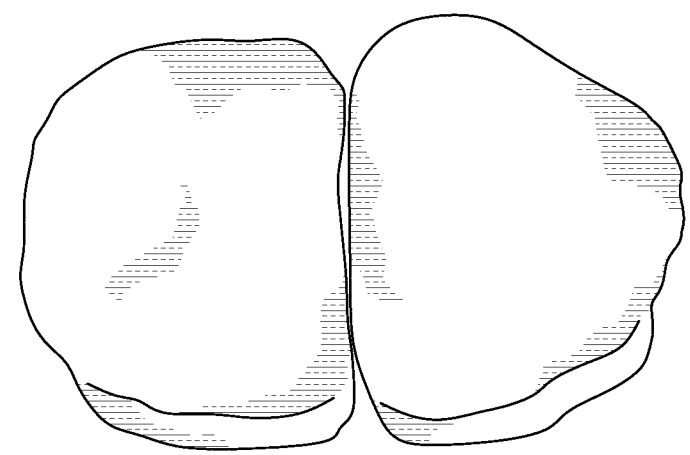
FIG. 6 is an illustrative view of the conceptual model—2 prosthetic "D" shaped devices in accordance with the present invention.
Figure 7:
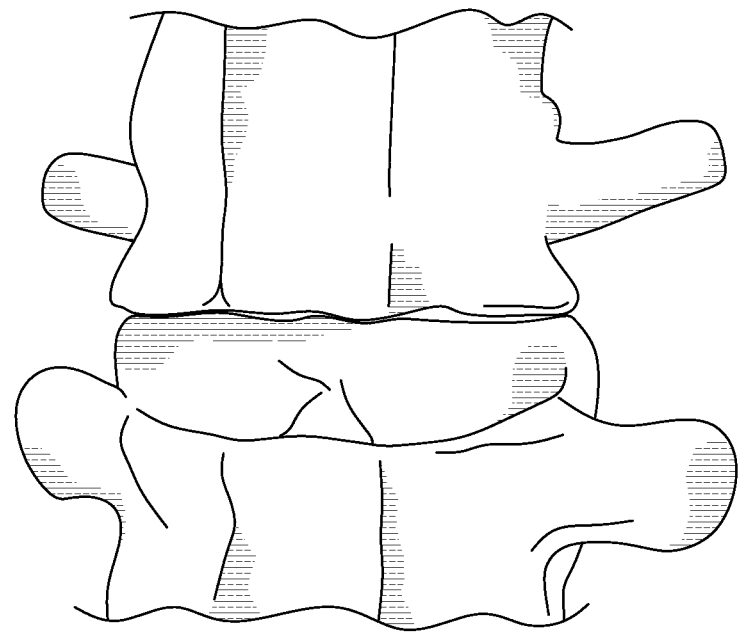
FIG. 7 is an illustrative view of the conceptual model from the anterior aspect in accordance with the present invention.
Figure 8:
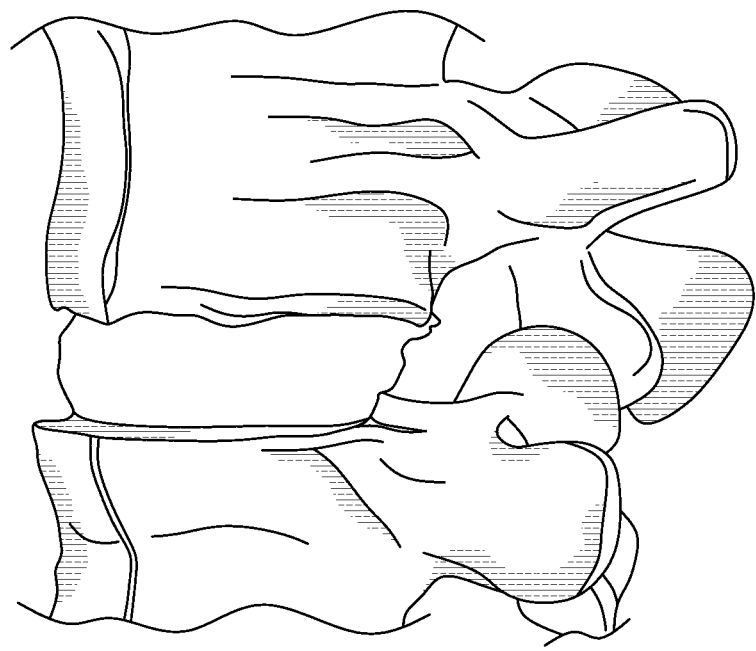
FIG. 8 is an illustrative view of the conceptual model from the left lateral aspect in accordance with the present invention, illustrating the maintenance of lordotic curve.

The preferred embodiment consists of woven and layered biologic fibers that create an annulus retaining the hydraulic element. The fabric orientation in the annular aspect is approximately 30 degrees with respect to the horizontal while at the endplates are 90 degrees with respect to each other. Additionally, the upper and lower woven or layered ends may be connected together through axial fibers. The fibers limit axial expansion of the hydraulic center element. The fabric element also can be of a variety of three dimensional shapes. These shapes can be approximately triangular with the longer length on the anterior aspect, as illustrated in FIG. 4. Such a shape would ensure maintenance of lumbar lordosis. The hydraulic element consists of an elastic material such as hydrogel, of a biological origin, in the form of beads. Under compression from the vertebral endplates the beads exert a radial pressure on the retaining fabric. The retaining fabric stretches in tension to balance the pressure transmitted by the beads. This is much the same way the natural disc functions. Additionally, the device allows 6 degrees of freedom, as the natural disc which provides limited translations in the axial, lateral, and anterior-posterior (AP) directions as well as rotations about those directions. Fixation of the device may be accomplished by a variety of means. These means may include, but are not limited to, one or more of the following: osteoincorporation through application of osteoconductive and/or osteoconductive substances; mechanical through staples, nails, buttons, or other fastening methods known in the art applied to the fabric tabs, as shown in FIG. 3, or chemical and/or biochemical means such as adhesives.

The method is conversion of the device to fusion and involves the bead arrangement and properties. The arrangement allows for the device to become a fusion element by virtue of the bead interstitial spaces. The bead properties allow the beads to be removed in part or in full and replaced by bone forming material. Removal of the hydraulic element is accomplished through vacuum. The mechanical properties of the hydraulic element beads is such that the shear force of vacuum in a cannulated needle exceeds that of the hydraulic element material. The fabric arrangement allows delivery of bone forming materials to the bead area through the fabric much as a needle passes through fabric during sewing. The bone forming materials, delivered percutaneously, infiltrate the hydraulic element interstitial spaces contacting the upper and lower fabric layers through the beads. The upper and lower layers are already ossified due to the bone in-growth from the vertebral endplates. The bone forming materials harden to provide immediate or delayed stability. Other constituents in the bone forming materials begin the process of bone growth along the scaffold provided by the cured material. Osteoinductive, osteoconductive, autologous cells, and scaffold materials and substances may be used alone or in combination to insure bone growth. As such, the method in accordance with the present invention for conversion of disc device to a fusion mass is inherent in the device design. However, certain combinations and formulations of the bone forming materials are necessary for success.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for the conversion of a spine disc prosthesis device to a fusion device comprising the steps of:
    accessing a patient's intervertebral disc space occupied by a disc prosthesis, the disc prosthesis comprising a plurality of dehydrateable hydraulic beads encompassed within a fabric constraining envelope, the disc prosthesis replacing both an annulus fibrosus and a nucleus pulposus of an intervertebral spinal disc;
    removing at least some of the dehydrateable hydraulic beads from the fabric constraining envelope to vacate a predetermined amount of space therein;
    injecting bone forming materials inside the fabric constraining envelope of the spine disc prosthesis; and
    maintaining the patient's spine in a stabilized position.

2. The method of claim 1 wherein substantially all of the dehydrateable hydraulic beads are removed.

3. The method of claim 1 wherein the bone forming material is selected from the group consisting of bone morphogenic proteins, demineralized bone matrix, aspirated autologous bone marrow, natural calcium phosphates, and synthetic calcium phosphates.

4. The method of claim 1 wherein the bone forming material is selected from the group consisting of osteoinductive elements, osteoconductive elements, structural elements, and stem cell elements.

5. The method of claim 1 further comprising the step of injecting a substance inside the fabric constraining envelope to provide structural stability, the substance reducing relative motion between the disc prosthesis device and the bone forming materials.

6. The method of claim 1 wherein the step of removing the dehydrateable hydraulic beads is performed by using endoscopic means selected from the group consisting of endoscopic aspiration and endoscopic suction.

7. The method of claim 1 wherein the bone forming materials are injected percutaneously.

* * * * *